United States Patent
Brennan et al.

(10) Patent No.: US 10,500,589 B2
(45) Date of Patent: Dec. 10, 2019

(54) SELF ALIGNING WEDGE CONTAINER WITH ANTI-EVAPORATION TUBE

(71) Applicant: Siemens Healthcare Diagnostics Inc., Tarrytown, NY (US)

(72) Inventors: Joseph Brennan, Newark, DE (US); James Kegelman, Wilmington, DE (US); William Hudson, Bear, DE (US); Peter Gebrian, Townsend, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/771,770

(22) PCT Filed: Feb. 27, 2014

(86) PCT No.: PCT/US2014/019078
§ 371 (c)(1),
(2) Date: Aug. 31, 2015

(87) PCT Pub. No.: WO2014/134331
PCT Pub. Date: Sep. 4, 2014

(65) Prior Publication Data
US 2016/0016162 A1    Jan. 21, 2016

Related U.S. Application Data

(60) Provisional application No. 61/771,242, filed on Mar. 1, 2013.

(51) Int. Cl.
*B01L 3/00* (2006.01)
*G01N 35/10* (2006.01)

(52) U.S. Cl.
CPC .......... *B01L 3/508* (2013.01); *G01N 35/1002* (2013.01); *B01L 2200/025* (2013.01);
(Continued)

(58) Field of Classification Search
CPC .............. B01L 3/508; B01L 2200/025; B01L 2200/142; B01L 2300/0618; B01L 2300/08; B01L 2300/0858; G01N 35/1002
(Continued)

(56) References Cited

U.S. PATENT DOCUMENTS 2,744,649 A * 5/1956 Smith ................ B01L 3/508
215/390
4,634,575 A * 1/1987 Kawakami ............. G01N 35/04
221/198
(Continued)

FOREIGN PATENT DOCUMENTS

DE        195 36 789 A1    4/1997

OTHER PUBLICATIONS

PCT International Search Report and Written Opinion dated Jun. 17, 2014 (11 Pages).
(Continued)

*Primary Examiner* — Benjamin R Whatley

(57) ABSTRACT

A fluid container includes a container body configured to hold one or more fluids. The container body has a first side wall and an opposing second side wall. The fluid container also includes one or more container alignment features disposed on an outer surface of the first side wall and configured to self-align the container body with a datum. The fluid container also includes one or more anti-evaporation tube alignment mechanisms disposed on one or more inner surfaces of the container body and configured to self-align an anti-evaporation tube within the container body.

17 Claims, 7 Drawing Sheets

(52) U.S. Cl.
CPC . *B01L 2200/142* (2013.01); *B01L 2300/0618* (2013.01); *B01L 2300/08* (2013.01); *B01L 2300/0858* (2013.01)

(58) Field of Classification Search
USPC .......................................................... 422/547
See application file for complete search history.

(56) References Cited

U.S. PATENT DOCUMENTS

| | | | |
|---|---|---|---|
| 5,324,481 A * | 6/1994 | Dunn | B01L 9/06 422/547 |
| 5,632,399 A * | 5/1997 | Palmieri | B01L 3/50853 220/253 |
| 5,736,101 A | 4/1998 | Gianino | |
| 6,943,030 B2 | 9/2005 | Gebrian et al. | |
| 7,258,480 B2 | 8/2007 | Dunfee et al. | |
| 2005/0271550 A1* | 12/2005 | Talmer | B01L 3/5082 422/400 |
| 2006/0073072 A1 | 4/2006 | Rudloff et al. | |
| 2009/0202394 A1 | 8/2009 | Nguyen et al. | |
| 2012/0141341 A1* | 6/2012 | Bartfeld | B01L 3/5082 422/550 |

OTHER PUBLICATIONS

Extended EP Search Report dated Oct. 7, 2016 of corresponding European Application No. 14756917.2, 4 Pages.

\* cited by examiner

SELF ALIGNING WEDGE CONTAINER WITH ANTI-EVAPORATION TUBE

CROSS-REFERENCE TO RELATED APPLICATIONS

This application claims priority to U.S. provisional application Ser. No. 61/771,242 filed Mar. 1, 2013, which is incorporated herein by reference in its entirety.

TECHNOLOGY FIELD

The present invention relates in general to systems and methods for aligning containers and, more particularly, to systems and methods for aligning wedge containers and anti-evaporation tubes within the wedge containers in a server ring for in vitro diagnostics in a clinical analyzer.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples, have been loaded. The analyzer extracts a liquid sample from the vial and combines the sample with various reagent fluids (reagents) in special reaction cuvettes or tubes (referred to generally as reaction vessels).

In some conventional systems, reagents to be combined with samples are contained in wedge-shaped reagent containers (containers) held in storage areas, such as server rings. In these conventional systems, automated reagent probes are positioned within the reagent containers to perform various tasks, such as aspirating reagents from their respective reagent containers and sensing levels (e.g., capacitance level sensing) of reagents remaining in each of their respective reagent containers. Accurate alignment of the reagent containers may be needed, however, to ensure that the reagent probes are accurately positioned within the containers to perform their various tasks efficiently. In conventional systems, the reagent containers are manually loaded within the storage areas and the resulting initial alignment may not be accurate. Further, movement of the containers from their initial alignment positions may also cause the reagent probes to perform less efficiently and decrease system throughput.

In some conventional systems, evaporation tubes may be placed within the containers to reduce evaporation of the reagents. In these conventional systems, an operator must manually remove the bottle closure (e.g., open a container cap) and manually place the evaporation tubes in their containers, which increases operator workflow. Movement of the evaporation tubes within their respective containers may also cause the reagent probes to perform less efficiently, thereby decreasing system throughput.

SUMMARY

Embodiments of the present invention include a fluid container having a container body configured to hold one or more fluids and having a first side wall and an opposing second side wall and one or more container alignment features disposed on an outer surface of the first side wall and configured to self-align the container body with a datum. The fluid container also includes one or more anti-evaporation tube alignment mechanisms disposed on one or more inner surfaces of the container body and configured to self-align an anti-evaporation tube within the container body.

According to an embodiment, the container body is wedge shaped and configured to be held in a compartment of a reagent server ring having a first compartment wall and a second compartment wall. The one or more container alignment features are configured to apply a force to a first compartment wall to align the container body with the datum, the datum corresponding to a portion of the opposing second compartment wall.

According to one embodiment, the one or more container alignment features are configured to prevent the container body from moving greater than a threshold container displacement distance from an initial self-aligned container location. The one or more anti-evaporation tube alignment mechanisms are configured to prevent an anti-evaporation tube in the container body from moving greater than a threshold tube displacement distance from an initial self-aligned anti-evaporation tube location in the container body.

In one embodiment, the fluid container further includes a container opening in the container body. The one or more container alignment features are configured to self-align the container opening with the datum and prevent the container opening from moving greater than a threshold opening displacement distance from an initial self-aligned container opening location.

In an aspect of an embodiment, the one or more container alignment features include a convex outer surface extending from the first side wall of the container body.

In another embodiment, the one or more anti-evaporation tube alignment mechanisms include a pair of opposing anti-evaporation tube alignment mechanisms disposed on opposing inner surfaces of the container body. In an aspect of an embodiment, each opposing anti-evaporation tube alignment mechanism has concave surfaces configured to face the anti-evaporation tube in the container.

According to an embodiment, the one or more anti-evaporation tube alignment mechanisms include a container neck disposed at an upper portion of the container body and having an inner surface configured to receive a force from an upper portion of the anti-evaporation tube.

Embodiments of the present invention include a fluid container having a container body configured to hold one or more fluids. The container body has a first container side wall and an opposing second container side wall. The fluid container also includes one or more container alignment features disposed on an outer surface of the first container side wall and extending outward from the outer surface of the first container side wall. The one or more container alignment features are configured to self-align a portion of the container body with a datum corresponding to a location adjacent the opposing second container side wall.

According to an embodiment, the container body is configured to be held in a compartment of a reagent server ring having a first compartment wall and a second compartment wall. The one or more container alignment features are configured to apply a force to the first compartment wall to cause the opposing second container side wall to contact a portion of the second compartment wall and self-align the portion of the container body with the datum. The datum corresponds to a location of the portion of the second compartment wall.

According to another embodiment, the fluid container further includes a container opening in the container body. The one or more container alignment features are configured to self-align the container opening with the datum and prevent the container opening from moving greater than a threshold opening displacement distance from an initial self-aligned container opening location.

In one embodiment, at least one container alignment feature includes a convex outer surface extending from the outer surface of the first container side wall. In another embodiment, the at least one container alignment features are molded to the container.

Embodiments of the present invention include a fluid container having a container body configured to hold one or more fluids. The container body includes: (i) a container front wall; (ii) a container rear wall opposite the container front wall; (iii) a first container side wall extending between the container front wall and the container rear wall; and (iv) a second container side wall opposing the first container side wall and extending between the container front wall and the container rear wall. The fluid container also includes a first anti-evaporation tube alignment mechanism disposed on a first inner surface of the first container side wall and a second anti-evaporation tube alignment mechanism disposed on a second inner surface of the second container side wall. The first and second anti-evaporation tube alignment mechanisms are configured to self-align an anti-evaporation tube within the container body.

According to an embodiment, the first anti-evaporation tube alignment mechanism and the second anti-evaporation tube alignment mechanism are configured to prevent the anti-evaporation tube in the container body from moving greater than a threshold tube displacement distance from an initial self-aligned anti-evaporation tube location in the container body.

According to another embodiment, each of the first anti-evaporation tube alignment mechanism and the second anti-evaporation tube alignment mechanism includes a concave surface configured to face an outer convex surface of the anti-evaporation tube in the container.

In one embodiment, the first anti-evaporation tube alignment mechanism opposes the second anti-evaporation tube alignment mechanism and each anti-evaporation tube alignment mechanism is located a predetermined distance from at least one of (i) the container neck and (ii) a bottom surface of the container body to self-align the anti-evaporation tube within the container body.

In another embodiment, the fluid container further includes a container neck disposed at an upper portion of the container body. The first anti-evaporation tube alignment mechanism, the second anti-evaporation tube alignment mechanism, and the container neck are together configured to self-align the anti-evaporation tube within the container body.

According to one embodiment, the first anti-evaporation tube alignment mechanism, the second anti-evaporation tube alignment mechanism, and the container neck are together configured to align the anti-evaporation tube so that the anti-evaporation tube and a probe received by the anti-evaporation tube share a same center axis.

According to another embodiment, the first anti-evaporation tube alignment mechanism, the second anti-evaporation tube alignment mechanism, and the container neck are together configured to prevent an external device from contacting the anti-evaporation tube when the external device is received by the anti-evaporation tube.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

Figure 1:
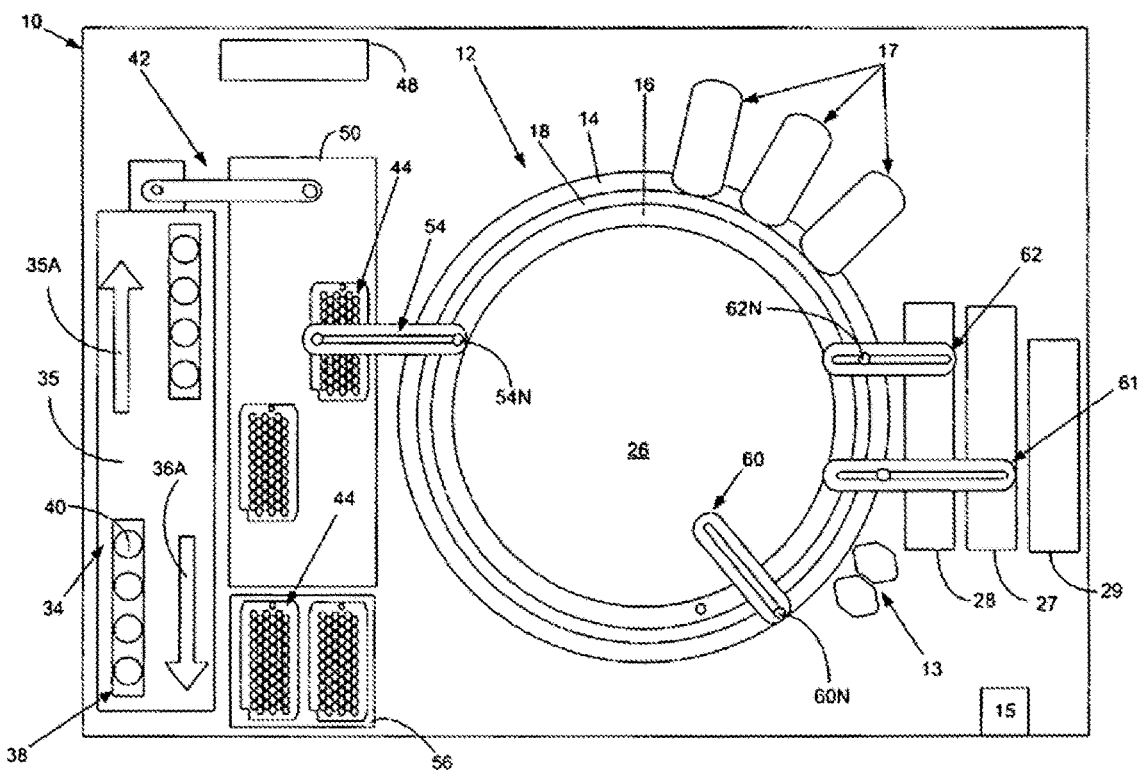
FIG. 1 is a top view of an exemplary chemistry analyzer in which embodiments of the vertical alignment and mixing method and apparatus may be employed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

EXEMPLARY EMBODIMENTS

Embodiments of the present invention include systems and methods that provide automated loading of self-aligning wedge containers in compartments of a server ring and self-aligning anti-evaporation tubes within the wedge containers. Embodiments of the present invention include containers having container alignment features that apply forces to walls of server ring compartments to self-align wedge containers with datums corresponding to opposing walls of the server ring compartments. Embodiments of the present invention utilize friction to prevent movement of the wedge containers greater than threshold distances from their initial self-aligned locations. Embodiments of the present invention utilize known force tolerances of the container alignment features to prevent movement of the containers from their initial self-aligned locations. Embodiments of the present invention include evaporation tube alignment mechanisms configured to self-align anti-evaporation tubes within container bodies to prevent evaporation tubes from moving greater than threshold distances. Embodiments of the present invention improve operator workflow by preventing movement of the evaporation tubes during transport and operation, thereby eliminating the need to manually place the evaporation tubes in the containers at the time of operation. Embodiments of the present invention prevent contact between the anti-evaporation tubes and the probes, thereby providing accurate positioning of the probes to perform their tasks and increasing throughput.

Figure 2:
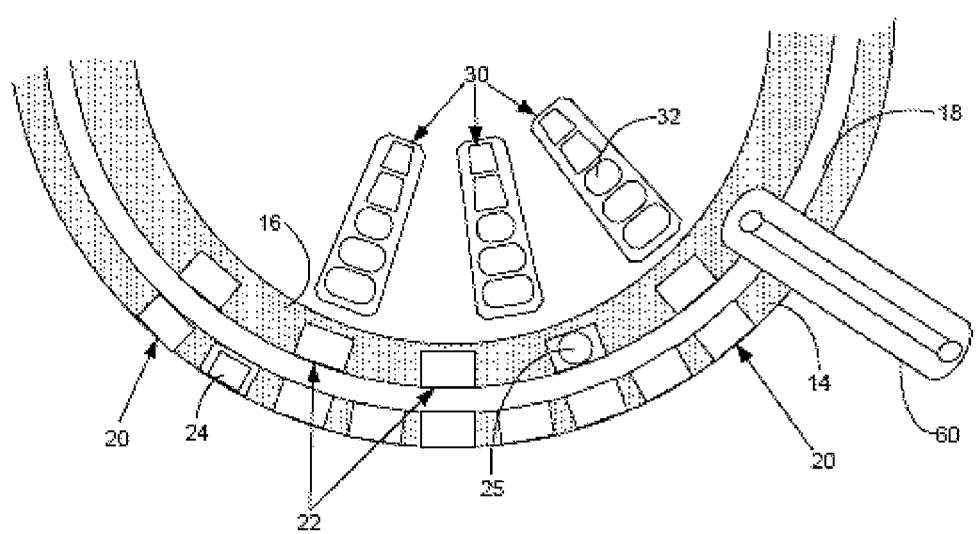
FIG. 2 is a top view of a portion of a carousel for transporting reaction vessels and cuvettes that can be used with the embodiments disclosed herein.

FIG. 1, taken with FIG. 2, shows schematically the elements of an automatic clinical chemistry analyzer (analyzer) 10 in which the present invention may be practiced, which may include, for instance the analyzer described in U.S. Pat. No. 7,258,480. Analyzer 10 comprises a reaction carousel 12 supporting an outer carousel 14 having cuvette ports 20 (represented in FIG. 2) formed therein and an inner carousel 16 having vessel ports 22 (represented in FIG. 2) formed therein, the outer carousel 14 and inner carousel 16 being separated by an open groove 18. Cuvette ports 20 are adapted to receive a plurality of reaction cuvettes 24, as represented in FIG. 2, that contain various reagents and sample liquids for conventional clinical chemistry and immunoassay assays. Vessel ports 22 can be adapted to receive a plurality of reaction vessels 25, as represented in FIG. 2, that contain specialized reagents for ultra-high sensitivity luminescent immunoassays. Cuvettes 24 and reaction vessels 25 can include bottom portions. While cuvettes and reaction vessels can have differing shapes, as used herein, the methods for mixing can be applied to the contents of reaction vessels 25 or cuvettes 24, and the terms reaction vessels and cuvettes should be considered broadly and interchangeably. Reaction vessels can include, for instance, cuvettes, vials, tubes, or other suitable vessels for mixing reagents and solutions.

Reaction carousel 12 is rotatable using stepwise movements in a constant direction, the stepwise movements being separated by a constant dwell time during which reaction carousel 12 remains stationary and computer controlled assay operational devices 13, such as sensors, reagent add stations, mixing stations, and the like, operate as needed on an assay mixture contained within a cuvette 24.

Analyzer 10 is controlled by software executed by a computer 15 based on computer programs written in a machine language like that used on the Dimension® clinical chemistry analyzer sold by Siemens Healthcare Diagnostics Inc. of Deerfield, Ill., and widely used by those skilled in the art of computer-based electromechanical control programming. Computer 15 also executes application software programs, such as the Dimension Vista® system software for performing assays conducted by various analyzing means 17 (e.g., detection units) within analyzer 10. Analyzing means 17 can include, for instance, one or more photometers, turbidimeters, nephelometers, electrodes, electromagnets, and/or LOCI® readers for interpreting the results of reactions within the reaction vessels 25 or cuvettes 24.

As seen in FIG. 1, a bi-directional incoming and outgoing sample fluid tube transport system 34 comprises a mechanism for transporting sample fluid tube racks 38 containing open sample fluid containers such as sample fluid tubes 40 from a rack input load position at a first end of the input lane 35 to the second end of input lane 35 as indicated by open arrow 35A. Liquid specimens contained in sample tubes 40 may be identified by reading bar coded indicia placed thereon using a conventional bar code reader to determine, among other items, a patient's identity, tests to be performed, if a sample aliquot is to be retained within analyzer 10, and, if so, for what period of time. It is also common practice to place bar coded or other indicia on sample tube racks 38 and employ a large number of bar code or other readers installed throughout analyzer 10 to ascertain, control, and track the location of sample tubes 40 and sample tube racks 38.

A conventional liquid sampling probe 42 is located proximate the second end of the input lane 35 and is operable to aspirate aliquot portions of sample fluid from sample fluid tubes 40 and to dispense an aliquot portion of the sample fluid into one or more of a plurality of vessels in aliquot vessel array 44. This provides a quantity of sample fluid to facilitate assays and to provide for a sample fluid aliquot to be retained by analyzer 10 within an environmental chamber 48. After sample fluid is aspirated from all sample fluid tubes 40 on a rack 38 and dispensed into aliquot vessels in array 44 and maintained in an aliquot vessel array storage and transport system 50, rack 38 may be moved, as indicated by open arrow 36A, to a front area of analyzer 10 accessible to an operator so that racks 38 may be unloaded from analyzer 10.

Sample aspiration probe 54 is controlled by computer 15 and is adapted to aspirate a controlled amount of sample from individual aliquot vessels in array 44 positioned at a sampling location within a track (not shown) and is then shuttled to a dispensing location where an appropriate amount of aspirated sample is dispensed into one or more cuvettes 24 for testing by analyzer 10 for one or more analytes. After sample has been dispensed into reaction cuvettes 24, conventional transfer means move aliquot vessel arrays 44, as required, within aliquot vessel array storage and dispensing module 56 between aliquot vessel array storage and transport system 50, environmental chamber 48, and a disposal area (not shown).

Temperature-controlled storage areas or servers 26, 27, and 28 contain an inventory of multi-compartment elongate reagent cartridges 30 (shown in FIG. 2) loaded into the system via input tray 29, such as those described in U.S. Pat.

No. 6,943,030 assigned to the assignee of the present invention. Cartridges 30 contain reagents in wells 32 to perform a number of different assays. Reagents may be moved and aligned within analyzer 10 by any conventional means, including those described in U.S. Patent Application Publication No. 2012/0127821, also assigned to the assignee of the present invention, and incorporated herein by reference. Computer 15 can control and track the motion and placement of the reagent cartridges 30. Reagents from server 26, 27, and 28 can be handled by one or more reagent probe arms 60, 61, and 62.

Although the containers in the embodiments described herein are reagent wedge containers configured to hold one or more reagent fluids in an IVD automation system, other embodiments may include containers having other geometries and configured to hold other types of fluids (e.g., samples). Embodiments may also include containers used in other types of environments.

Figure 3:
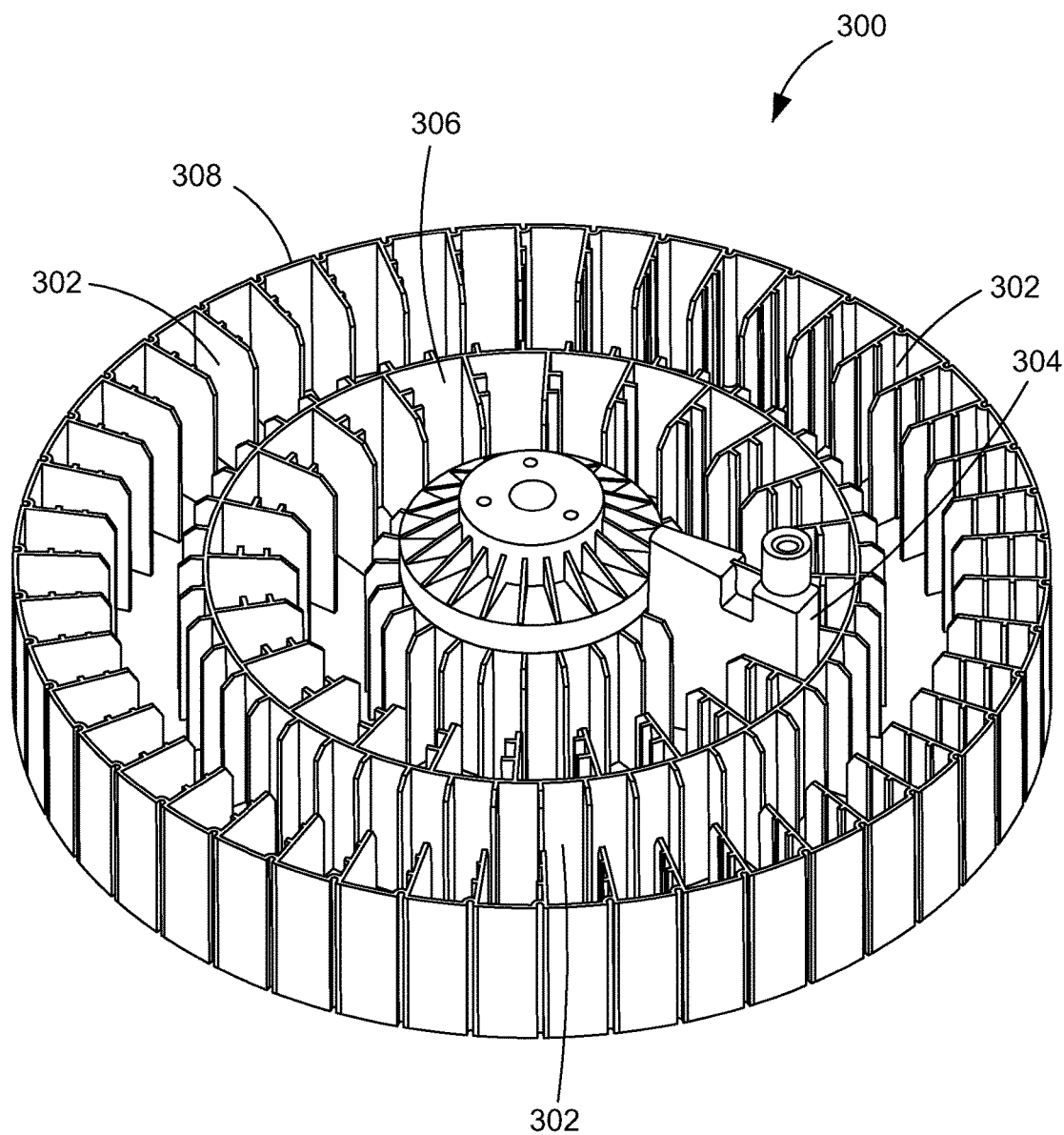
FIG. 3 is a perspective view of an exemplary server ring holding an exemplary container in a server ring compartment that can be used with the embodiments disclosed herein.

FIG. 3 is a perspective view of an exemplary server ring 300 having a plurality of compartments 302 for holding one or more containers, such as container 304. For simplicity, only one container 304 is shown in FIG. 3. In some embodiments, server ring 300 may hold any number of containers 304. In some embodiments, container 304 may be used to hold reagent fluids. In other embodiments, container 304 may be used to hold other fluids, such as patient samples. As shown in FIG. 3, the compartments 302 of a server ring 300 may be wedge-shaped and the container 304 may be wedge-shaped to fit securely within a corresponding compartment 302. Server ring 300 may be positioned at a center of a reaction carousel, such as at the center of the reaction carousel 12 shown in FIG. 1. In some embodiments, reagent server rings may be located on outer portions of carousels and the samples and/or cuvettes may be located on the inner portions of carousels. The server ring 300 shown in the embodiment in FIG. 3 includes an inner loop 306 and an outer loop 308. Embodiments may include any number of loops.

Figure 4:
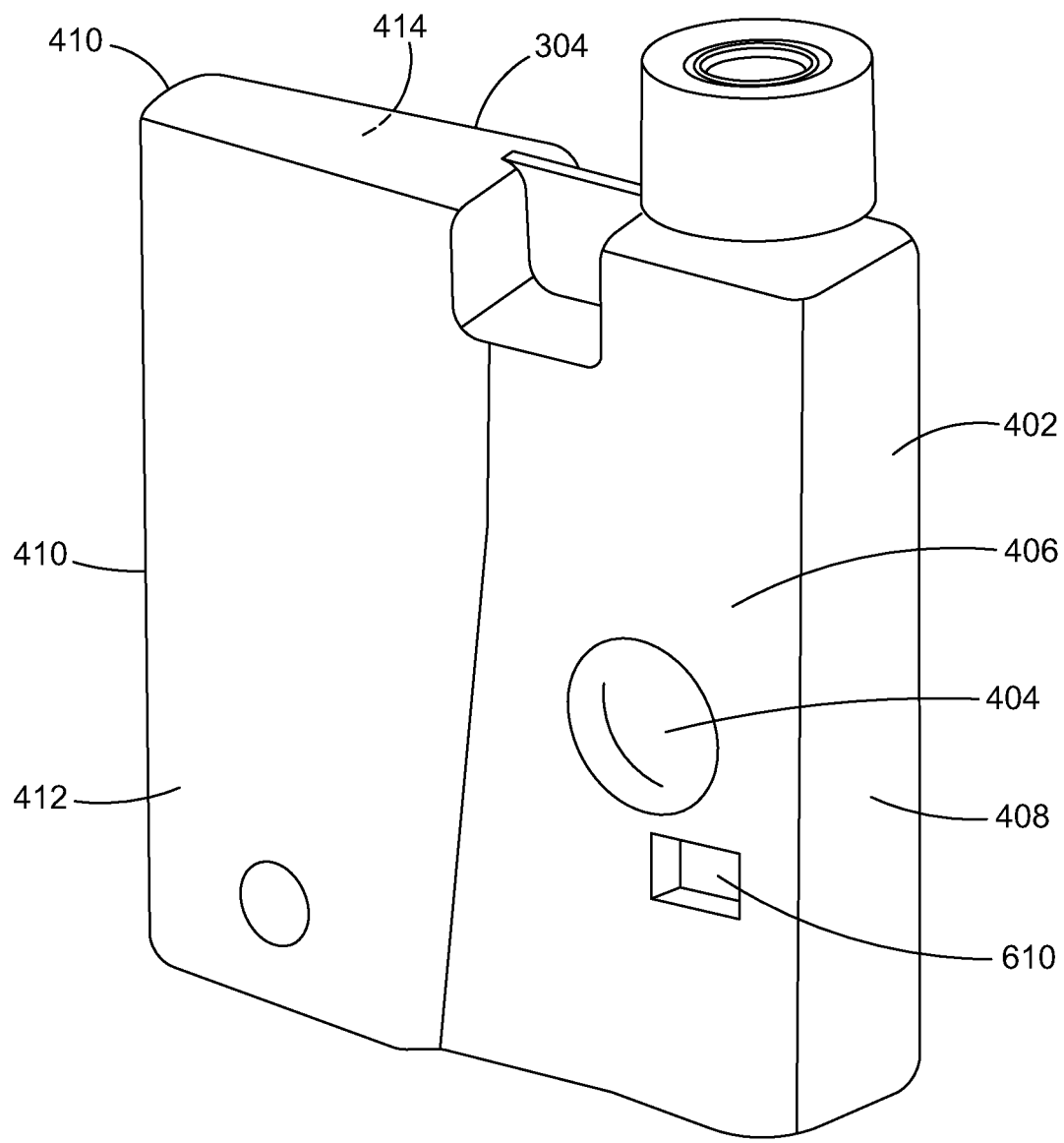
FIG. 4 is a perspective view of the container shown in FIG. 3 that can be used with the embodiments disclosed herein.

FIG. 4 is a perspective view of the fluid container 304 shown in FIG. 3. As shown, container 304 may include a container body 402 configured to hold one or more fluids (not shown). As shown, the container body 402 includes a container front wall 408, a container rear wall 410 opposing the container front wall 408, a first container side wall 412 and an opposing second container side wall 414. The first container side wall 412 and the opposing second container side wall 414 extend between the container front wall 408 and the container rear wall 410. A container alignment feature 404 shown in FIG. 4 is disposed on an outer surface 406 of the first container side wall 412 and is convex or dome-shaped extending from the outer surface 406 of first container side wall 412.

As described above, accurate alignment of the reagent containers may be needed to ensure that the reagent probes, such as reagent probe 702 (shown in FIG. 7), are accurately positioned within the containers to perform their various tasks efficiently. In conventional systems, the reagent containers are manually loaded within the storage areas and the resulting initial alignment may not be accurate. In automation systems that automatically load containers 304 into compartments 302, the probe 702 may be initialized to datums 505 (e.g., a physical location, notch, position or level) corresponding to portions of the compartments 302, such as second compartment walls 503 or protrusions 510 from those compartment walls. Embodiments may, however, include initializing the probe 702 to datums 505 corresponding to any portion of the compartments 302 or any portion of server ring 300. To ensure that the reagent probes 702 are accurately positioned within the containers 304, the system must be able to determine the location of a portion of each container 304, such as the container opening 504, relative to the datum 505. The container alignment feature 404 shown in the embodiments in FIG. 4 and FIG. 5 may be used to self-align container 304 within compartment 302, thereby providing the system with an accurate location of the container opening 504 relative to the datum 505 or any portion of the compartment 302 or server ring 300 to which the datum 505 corresponds. This accurate self-alignment provides for automatic loading of the self-aligning wedge container 304 in the compartment 302 by a loading device, such as a pick and place device (not shown).

Figure 5:
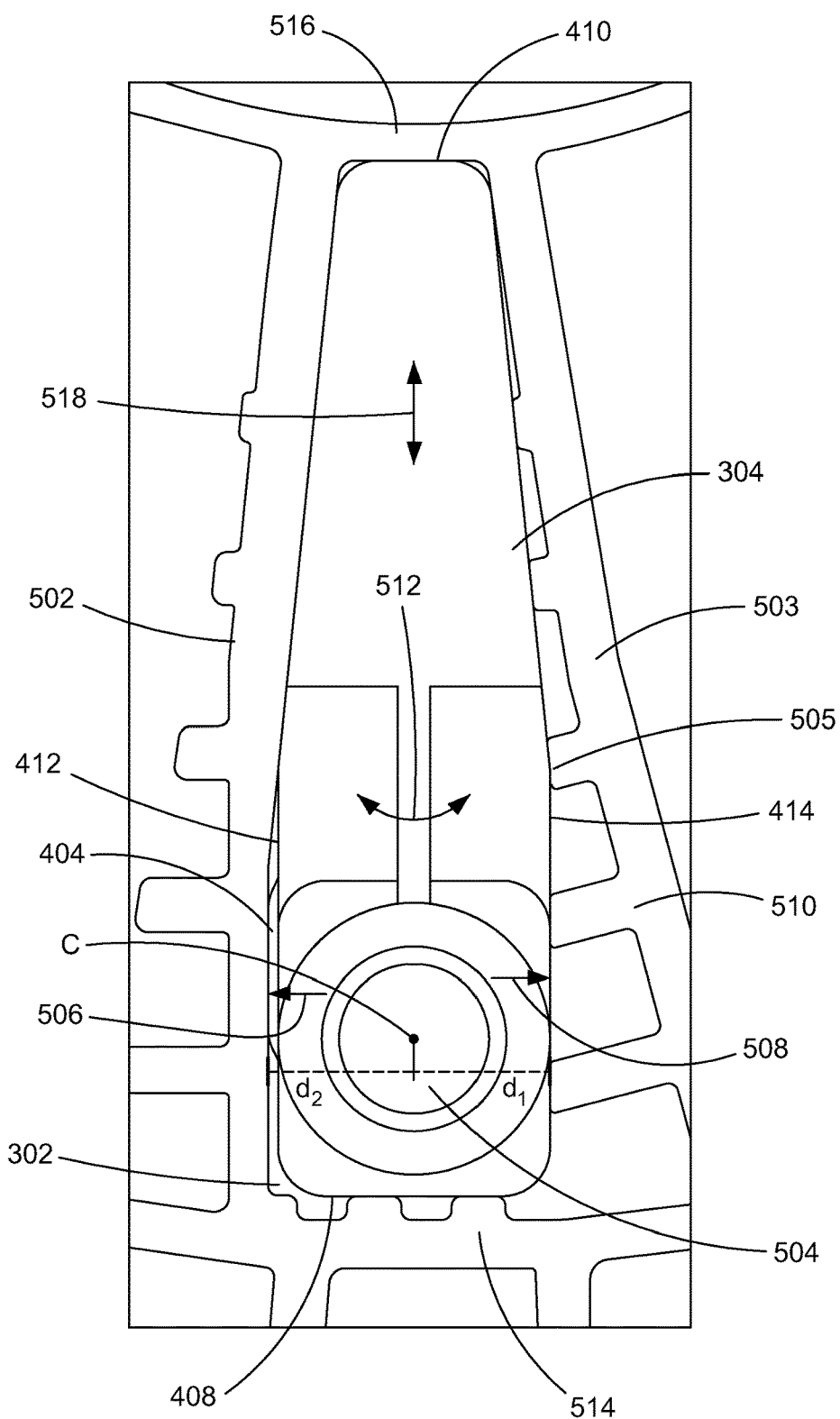
FIG. 5 is a top view of the container shown in FIG. 3 illustrating a container alignment feature in contact with a side wall of a compartment of the server ring that can be used with the embodiments disclosed herein.

FIG. 5 is a top view of the container 304 shown in an initial alignment location within compartment 302 having a first compartment wall 502 and an opposing second compartment wall 503. As shown, container 304 may be in its initial alignment position when a portion of the container alignment feature 404 is in contact with an inner surface of side wall 502 of the compartment 302 and the opposing second container side wall 414 is in contact with a portion of the opposing second compartment wall 503. In the embodiment shown in FIG. 5, the center c of opening 504 of the container 304 may be aligned with a datum 505 corresponding to edges of protrusions 510. In other embodiments, the center c of opening 504 of container 304 may be aligned with datums corresponding to any portions of second compartment walls 503. For example, in some embodiments, second compartment walls 503 may not include any protrusions 510 and the opening 504 of container 304 may be aligned with datums 505 corresponding directly to edges of the second compartment walls 503. Embodiments may also include aligning any portions of containers 304 with datums corresponding to any portion of the server ring 300 or compartments 302 of the server ring 300, such as the first compartment wall 502.

In some embodiments, when container 304 is in an initial alignment position within a compartment 302, the location of a container opening 504 may be determined from the distance d1 between the center c of the opening 504 and the second compartment wall 503. As described above, however, embodiments may also include alignment with datums corresponding to any portion of the compartments 302 of the server ring 300, such as the first compartment wall 502. Accordingly, in some embodiments, a distance d2 between the center c of the container opening 504 and a position corresponding to the first compartment wall 502 may be determined. In other aspects, opening locations may be determined from the distances between any server ring component or system component and any portion of a container (e.g., an outer surface of the container body 402, a perimeter of the container opening 504, a center c of the container opening 504, etc.). In other aspects, opening locations may be determined from the distances between openings of different containers.

In the embodiment shown in FIG. 5, the container alignment feature 404 may apply forces, indicated by arrows 506 and 508 to first and second walls 502 and 503, respectively, of server ring compartments 302 and utilize friction between the containers 304 and the compartment walls 502 and 503 to self-align the wedge container 304 with datum 505 corresponding to the location of the second wall 503 of the server ring compartment 302. For example, in the initial alignment position shown in FIG. 5, a spring force may be applied by container alignment feature 404 to first compartment wall 502 in the direction indicated by arrow 506. This spring force may also cause the container 304 to apply an opposing force to the protrusions 510 of opposing side wall 503 in the direction indicated by arrow 508, providing friction between the container 304 and the compartment walls 502 and 503 to self-align the container 304 with datum 505 corresponding to the location of the second wall 503 of the server ring compartment 302.

Figure 7:
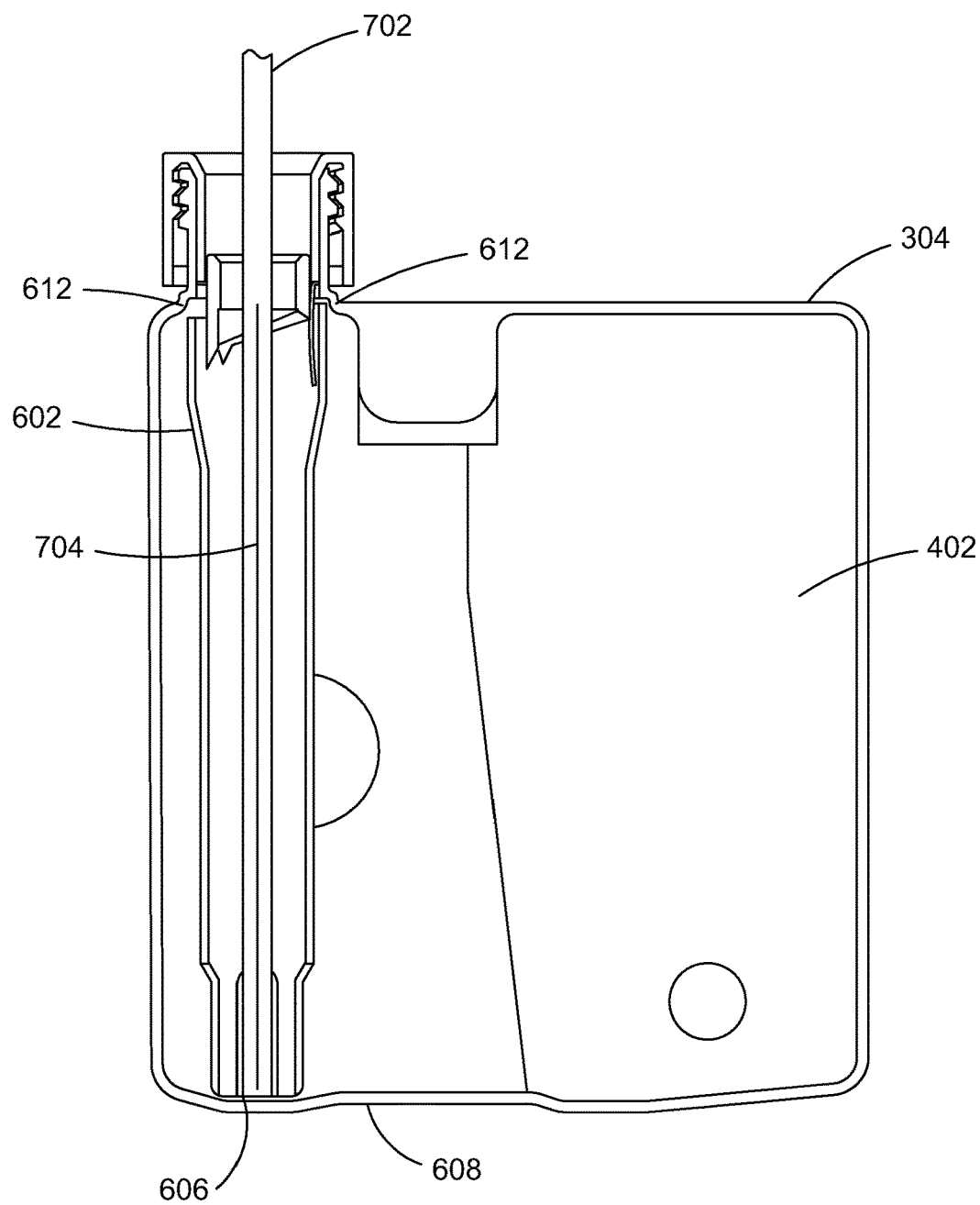
FIG. 7 is a side cross-sectional view of the container shown in FIG. 3 illustrating a reagent probe positioned within the anti-evaporation tube that can be used with the embodiments disclosed herein.

Movement of the container 304 and movement of the container opening 504 within the compartment 302 may occur due to spring force tolerances of the container alignment feature 404. Some movement of the container opening 504 from its original location when the container 304 is in its initial alignment position may, however, be permitted, provided that the movement allows the reagent probe 702 to be positioned accurately through the opening 504 and within the container 304, as shown in FIG. 7. If certain variables are known, such as the spring force tolerance of the container alignment feature 404 and the geometry and tolerances of the container 304 and compartment 302, then a distance d1 between the center c of the container opening 504 and the datum 505 corresponding to the second compartment wall 503 may be determined. Accordingly, the location of the center c of the container opening 504 relative to the datum 505 may be determined to ensure that the reagent probe 702 is accurately positioned within the container 304 to perform its various tasks efficiently. Tolerances of container alignment features 404 may be determined for example, from repeated analysis on the same container alignment features that produce similar results.

The container alignment feature 404 may also prevent substantial movement of the container 304 within the compartment 302. That is, the forces applied in the directions indicated by arrows 506 and 508 by the container alignment feature 404 causes friction between the containers 304 and the compartment walls 502 and 503, thereby preventing substantial movement of the container 304 within the compartment 302. The amounts of spring force applied to container 304 and the resulting friction may depend on variables such as, for example, the material, location, and geometry of the container alignment feature 404. In some embodiments, the container alignment feature 404 and the first container side wall 412 together may apply the spring force to first compartment wall 502. For example, if the container alignment feature 404 and the first container side wall 412 are molded together, the container alignment feature 404 and the first container side wall 412 may each apply its own force to produce a combined spring force to first compartment wall 502.

In some embodiments, a container alignment feature 404 may be configured to prevent the container opening 504 from moving more than a threshold displacement distance from its initial location. In some aspects, the threshold distance may be a predetermined distance that is based on the geometries of the system components, such as the geometries of the probe 702, the container 304, and the container opening 504. In some aspects, substantial movement may be determined as movement in one or more directions. For example, substantial movement may be determined as movement in an angular direction, as indicated by arrows 512.

The geometry of the container alignment feature 404 shown in FIG. 4 and FIG. 5 is merely exemplary. Embodiments may include other container alignment features having different geometries and at different locations that are configured to apply forces to external objects in contact with the containers and/or configured to prevent container openings from moving greater than threshold displacement distances from the initial container opening locations. Some embodiments may include containers having multiple container alignment features on an outer surface of a container side wall. In some embodiments, container alignment features may include flexible materials, such as plastics, and may be unitarily molded or separately molded with the containers. Container alignment features and containers may be formed from the same material or different materials.

In addition to preventing substantial movement in an angular direction 512, the container 304 may be configured to prevent substantial movement in a radial direction, indicated by arrows 518. For example, as shown in FIG. 5, the container 304 is configured such that front wall 408 is in contact with compartment front wall 514 and container rear wall 410 is in contact with compartment rear wall 516 to prevent substantial movement in the radial direction, indicated by arrows 518. In some embodiments, one or more container alignment features 404 may be located on the container front wall 408 and/or the container rear wall 410 to prevent substantial movement in the radial direction. In some aspects, one or more container alignment features 404 may be configured to prevent substantial movement in any direction (e.g., angular direction, radial direction, and any direction having an angular or radial component). In some embodiments, one or more compartment walls 502, 503, 514, 516 may include mating features (e.g., concave features opposing the convex container alignment features 404) configured to receive the one or more convex shaped container alignment features 404 to prevent substantial movement of the container 304 relative to the compartment walls 502, 503, 514, 516 in any direction.

Figure 6A:
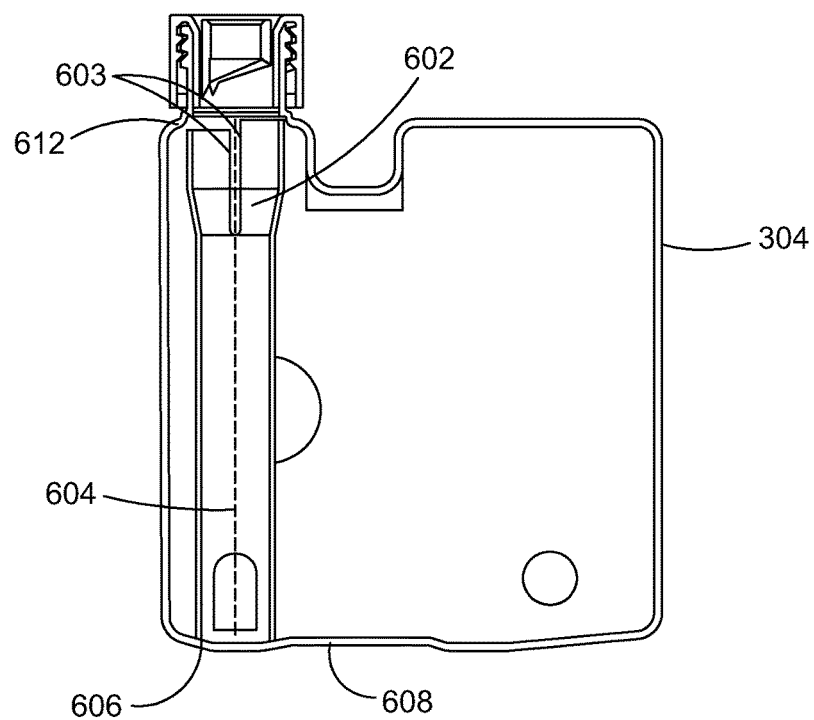
FIG. 6A is a side cross-sectional view of the container shown in FIG. 3 illustrating an anti-evaporation tube positioned in the container that can be used with the embodiments disclosed herein.
Figure 6B:
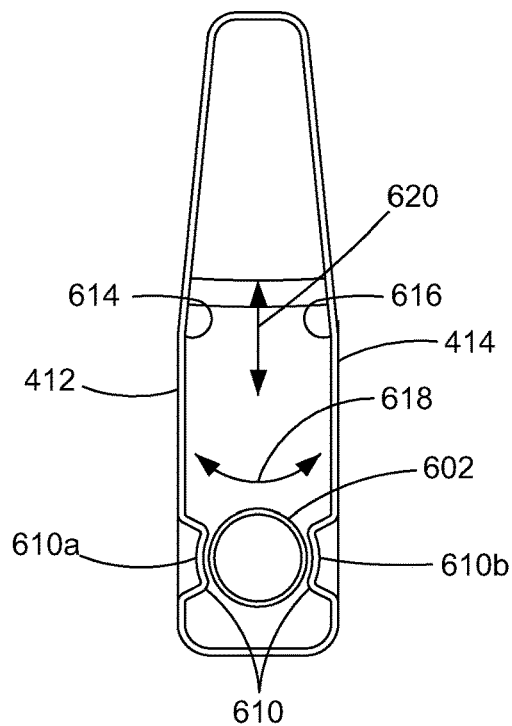
FIG. 6B is a top cross-sectional view of the container shown in FIG. 3 illustrating a pair of anti-evaporation tube alignment mechanisms in the container that can be used with the embodiments disclosed herein.

FIG. 6A is a side cross-sectional view of the container 304 illustrating an anti-evaporation tube 602 positioned in the container 304. FIG. 6B is a top cross-sectional view of the container 304 illustrating a pair of anti-evaporation tube alignment mechanisms 610 in the container 304. FIG. 7 is a side cross-sectional view of the container 304, illustrating a reagent probe 702 positioned within the anti-evaporation tube 602.

In some embodiments, other objects, such as anti-evaporation tube 602, may be accurately aligned within containers 304. For example, as shown in FIG. 6A, anti-evaporation tube 602 may be positioned in the container 304 to reduce evaporation of fluids from the container 304. In some embodiments, anti-evaporation tube 602 may include opposing slots 603 (shown in FIG. 6A) that are configured to allow anti-evaporation tube 602 to be inserted into container 304 and be locked into the position shown in FIG. 6A. For example, the slots 603 may allow one or more portions of the anti-evaporation tube 602 proximate to the slots 603 to bend inward during insertion and retract back after insertion and provide friction against an inner surface of container neck 612 to lock the anti-evaporation tube 602 into the position shown in FIG. 6A. Embodiments may include any number of slots having different geometries and at any locations on anti-evaporation tubes.

In some embodiments, container 304 may include a low portion 606 of container bottom floor 608 that includes a portion of the remaining fluids in the container 304. Aspiration of the remaining fluids in container 304 may be performed more efficiently if reagent probe 702 is accurately positioned at low spot 606 of the container 304. If anti-evaporation tube 602 is not accurately aligned within the container 304, however, when reagent probe 702 is positioned in the container 304, reagent probe 702 may contact the anti-evaporation tube 602 and not be accurately positioned at low spot 606.

In some embodiments, anti-evaporation tube alignment mechanisms 610a, 610b may be disposed on one or more inner surfaces of the container 304 and be configured to self-align an anti-evaporation tube 602 within the container 304. As shown in FIG. 7, the anti-evaporation tube 602 is self-aligned within the container such that the anti-evaporation tube 602 and probe 702 share the same center axis 704 when probe 702 is received by the anti-evaporation tube 602. Accordingly, the anti-evaporation tube 602 is accurately aligned so that probe 702 does not contact the anti-evaporation tube 602 when probe 702 is automatically positioned at low portion 606 of container bottom floor 608 to aspirate the remaining fluids at low portion 606. Further, the anti-evaporation tube alignment mechanisms 610a, 610b are configured to prevent the anti-evaporation tube 602 from moving from its initial alignment position during operation and/or transport.

As shown in the embodiment in FIG. 6B, container 304 includes a first anti-evaporation tube alignment mechanism 610a disposed on a first inner surface 614 of the first container side wall 412 and a second anti-evaporation tube alignment mechanism 610b disposed on a second inner surface 616 of the second container side wall 414. First anti-evaporation tube alignment mechanism 610a and second anti-evaporation tube alignment mechanism 610b each comprise a concave surface configured to face an outer convex surface of the anti-evaporation tube 602 in the container 304. The geometry of the anti-evaporation tube alignment mechanism 610a and 610b shown in FIG. 6B is merely exemplary. Embodiments may include anti-evaporation tube alignment mechanisms having different geometries. The concave surfaces of anti-evaporation tube alignment mechanisms 610a and 610b shown in FIG. 6B may prevent anti-evaporation tube 602 in the container 304 from moving in an angular direction, indicated by arrows 618, and in a radial direction, indicated by arrows 620.

In some embodiments, anti-evaporation tube alignment mechanisms may be positioned to oppose each other within the container. For example, as shown in the embodiment in FIG. 6B, the first anti-evaporation tube alignment mechanism 610a may oppose the second anti-evaporation tube alignment mechanism 610b. Embodiments may include anti-evaporation tube alignment mechanisms that do not oppose each other. Embodiments may include any number of anti-evaporation tube alignment mechanisms disposed at any locations on the containers.

Anti-evaporation tube alignment mechanism 610 may also prevent anti-evaporation tube 602 from moving greater than a threshold tube displacement distance from its initial anti-evaporation tube location in the container 304. In some aspects, the threshold tube displacement distance may be a predetermined distance measured from a center axis 604 of the anti-evaporation tube 602 at the initial center axis location.

In some embodiments, container 304 may also include a container neck 612 disposed at an upper portion of the container body 402, as shown in FIG. 7. The neck 612 may be configured to self-align the anti-evaporation tube within the container 304 and/or prevent the anti-evaporation tube 602 in the container 304 from moving greater than the threshold tube displacement distance from the initial anti-evaporation tube location in the container 304. For example, as shown in FIG. 6A and FIG. 7, anti-evaporation tube 602 may be in contact with container neck 612, thereby limiting movement of the upper portion of anti-evaporation tube 602. In some embodiments, container neck 612, first anti-evaporation tube alignment mechanism 610a, and second anti-evaporation tube alignment mechanism 610b together may self-align the anti-evaporation tube within the container 304 and/or prevent substantial movement of the anti-evaporation tube 602 from its initial alignment location, thereby preventing the reagent probe 702 from contacting the anti-evaporation tube 602.

In some embodiments, anti-evaporation tube alignment mechanisms may be located at predetermined distances from the container necks and/or bottom surfaces of the containers to self-align the anti-evaporation tubes within the containers and prevent movement of the anti-evaporation tubes. For example, anti-evaporation tube alignment mechanism 610 may be located at the position shown in FIG. 4. The distances may be determined by a number of variables, including the geometries of the containers, the geometries of the anti-evaporation tubes, and the number of anti-evaporation tube alignment mechanisms.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A fluid container comprising:
   a) a wedge shaped container body comprising a rigid first side wall and an opposing second side wall, wherein the container body is configured to hold one or more fluids;
   b) one or more container alignment features comprising a flexible convex outer surface disposed on and extending outwardly from an outer surface of the first side wall of the container body;
   wherein, when the fluid container is held in a compartment of a reagent server ring comprising a first compartment wall, an opposing second compartment wall, and a protrusion from the second compartment wall, the flexible convex outer surface applies a spring force to the first compartment wall and aligns the fluid container with the protrusion from the second compartment wall; and
   c) one or more anti-evaporation tube alignment mechanisms comprising a concave inner surface disposed on and extending inwardly from one or more inner surfaces of the first and second side walls and configured to self-align an anti-evaporation tube within the container body along a length of the anti-evaporation tube.

2. The fluid container of claim 1, wherein the one or more container alignment features are configured to prevent the container body from moving greater than a threshold container displacement distance from an initial self-aligned container location, and
   the one or more anti-evaporation tube alignment mechanisms are configured to prevent an anti-evaporation tube in the container body from moving greater than a threshold tube displacement distance from an initial self-aligned anti-evaporation tube location in the container body.

3. The fluid container of claim 1, further comprising a container opening in the container body,
   wherein the one or more container alignment features are configured to self-align the container opening with the protrusion and prevent the container opening from moving greater than a threshold opening displacement distance from an initial self-aligned container opening location.

4. The fluid container of claim 1, wherein the one or more anti-evaporation tube alignment mechanisms comprise:
a pair of opposing anti-evaporation tube alignment mechanisms disposed on opposing inner surfaces of the first and second side walls.

5. The fluid container of claim 4, wherein each opposing anti-evaporation tube alignment mechanism has concave surfaces configured to face the anti-evaporation tube in the container.

6. The fluid container of claim 1, wherein the one or more anti-evaporation tube alignment mechanisms comprise a container neck disposed at an upper portion of the container body and having an inner surface configured to receive a force from an upper portion of the anti-evaporation tube.

7. A fluid container comprising:
a wedge shaped container body configured to hold one or more fluids, the container body comprising a rigid first container side wall and an opposing second container side wall; and
one or more container alignment features comprising a flexible convex outer surface disposed on and extending outward from an outer surface of the first container side wall of the container body;
wherein, when the fluid container is held in a compartment of a reagent server ring comprising a first compartment wall, an opposing second compartment wall, and a protrusion from the second compartment wall, the flexible convex outer surface applies a spring force to the first compartment wall and aligns the fluid container with the protrusion from the second compartment wall.

8. The fluid container of claim 7, wherein the container body is configured to be held in a compartment of a reagent server ring having a first compartment wall and a second compartment wall.

9. The fluid container of claim 7, further comprising a container opening in the container body,
wherein the one or more container alignment features are configured to self-align the container opening with the protrusion and prevent the container opening from moving greater than a threshold opening displacement distance from an initial self-aligned container opening location.

10. The fluid container of claim 7, wherein the at least one container alignment feature is molded from the first container side wall.

11. A fluid container comprising:
a wedged shaped container body configured to hold one or more fluids, the container body comprising: (i) a container front wall; (ii) a container rear wall opposite the container front wall; (iii) a rigid first container side wall extending between the container front wall and the container rear wall; and (iv) a second container side wall opposing the first container side wall and extending between the container front wall and the container rear wall;
one or more container alignment features comprising a flexible convex outer surface disposed on and extending outwardly from an outer surface of the first side wall of the container body;
a first anti-evaporation tube alignment mechanism comprising a concave inner surface disposed on and extending inwardly from a first inner surface of the first container side wall; and
a second anti-evaporation tube alignment mechanism comprising a concave inner surface disposed on and extending inwardly from a second inner surface of the second container side wall;
wherein, when the fluid container is held in a compartment of a reagent server ring comprising a first compartment wall, an opposing second compartment wall, and a protrusion from the second compartment wall, the flexible convex outer surface applies a spring force to the first compartment wall and aligns the fluid container with the protrusion from the second compartment wall; and
wherein the first and second anti-evaporation tube alignment mechanisms are configured to self-align an anti-evaporation tube within the container body along a length of the anti-evaporation tube.

12. The fluid container of claim 11, wherein the first anti-evaporation tube alignment mechanism and the second anti-evaporation tube alignment mechanism are configured to prevent the anti-evaporation tube in the container body from moving greater than a threshold tube displacement distance from an initial self-aligned anti-evaporation tube location in the container body.

13. The fluid container of claim 11, wherein the first anti-evaporation tube alignment mechanism and the second anti-evaporation tube alignment mechanism each comprise a concave surface configured to face an outer convex surface of the anti-evaporation tube in the container.

14. The fluid container of claim 11, further comprising a container neck disposed at an upper portion of the container body, and
wherein the first anti-evaporation tube alignment mechanism, the second anti-evaporation tube alignment mechanism, and the container neck are together configured to self-align the anti-evaporation tube within the container body.

15. The fluid container of claim 14, wherein the first anti-evaporation tube alignment mechanism opposes the second anti-evaporation tube alignment mechanism and each anti-evaporation tube alignment mechanism is located a predetermined distance from at least one of (i) the container neck and (ii) a bottom surface of the container body to self-align the anti-evaporation tube within the container body.

16. The fluid container of claim 14, wherein the first anti-evaporation tube alignment mechanism, the second anti-evaporation tube alignment mechanism, and the container neck are together configured to align the anti-evaporation tube so that the anti-evaporation tube and a probe received by the anti-evaporation tube share a same center axis.

17. The fluid container of claim 14, wherein the first anti-evaporation tube alignment mechanism, the second anti-evaporation tube alignment mechanism, and the container neck are together configured to prevent a reagent probe from contacting the anti-evaporation tube when the reagent probe is received by the anti-evaporation tube.

* * * * *